United States Patent [19]

Michel et al.

[11] Patent Number: 4,902,789
[45] Date of Patent: Feb. 20, 1990

[54] PROCESS AND COMPOSITION FOR THE PURIFICATION OF AMPHOTERICIN B

[75] Inventors: Gerd W. Michel, Princeton; Wilbur L. Bryan, Somerset, both of N.J.; Elizabeth Bryan, Arlington, Va.

[73] Assignee: E. R. Squibb & Sons, Inc., Princeton, N.J.

[21] Appl. No.: 113,790

[22] Filed: Oct. 27, 1987

[51] Int. Cl.$^4$ .................... C07H 17/08; A01N 43/04; A61K 35/00; C07G 3/00
[52] U.S. Cl. .................... 536/6.5; 536/17.2; 536/18.5; 514/31; 424/123; 424/119; 424/118
[58] Field of Search .................... 536/6.5, 4.1, 17.2; 514/31; 424/123, 118, 119

[56] References Cited

U.S. PATENT DOCUMENTS

| | | |
|---|---|---|
| 2,908,611 | 10/1959 | Dutcher et al. |
| 3,965,090 | 6/1976 | Metzger .................... 536/6.5 |
| 4,049,898 | 9/1977 | Metzger .................... 536/6.5 |
| 4,054,265 | 10/1977 | Metzger . |
| 4,054,734 | 10/1977 | Metzger .................... 536/6.5 |
| 4,177,265 | 12/1979 | Michel et al. . |
| 4,308,375 | 12/1981 | Tang . |

OTHER PUBLICATIONS

*The Journal of Antibotic*, vol. XXVIII, No. 3, Mar. 1975, p. 244, Falkowski, L., "N–Glycosyl Derivatives of Polyene Macrolide Antibiotics".

*Primary Examiner*—Ronald W. Griffin
*Assistant Examiner*—Everett White
*Attorney, Agent, or Firm*—Theodore R. Furman, Jr.

[57] ABSTRACT

A unique four-solvent system comprising methanol, dimethylformamide, methylene chloride and water is employed to provide an improved process for the purification and crystallization of amphotericin B.

10 Claims, No Drawings

PROCESS AND COMPOSITION FOR THE PURIFICATION OF AMPHOTERICIN B

FIELD OF THE INVENTION

The present invention relates to a process and composition for the purification and crystallization of amphotericin B.

BACKGROUND OF THE INVENTION

Amphotericin B, a potent antifungal agent, is a member of a class of compounds known as polyene macrolide antibiotics. These compounds are characterized by a large lactone ring which includes a chain of conjugated double bonds.

Amphotericin B, and its method of preparation from *Streptomyces nodosus*, is disclosed by Dutcher et al. in U.S. Pat. No. 2,908,611, issued October 13, 1959. The structure of amphotericin B is now known to be

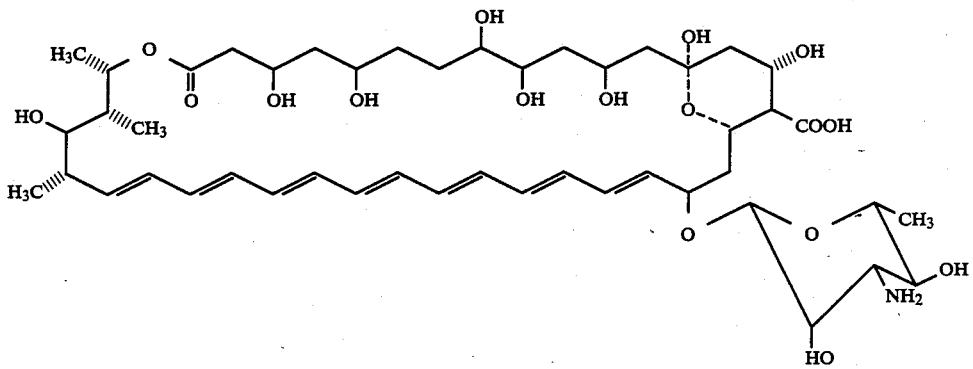

The processes disclosed by Dutcher et al. for extraction and crystallization of amphotericin involve:

a. slurrying the crude amphotericin in an alcohol with an acid and thereafter neutralizing with a strong base; or b. slurrying the crude amphotericin with dimethylformamide and treating this with an aqueous alcohol or aqueous ketone.

Michel et al. in U.S. Pat. No. 4,177,265 disclose a process for the purification of amphotericin B which utilizes a solubilizing media comprising sodium iodide or sodium thiocyanate and acetone or methanol. The use of any one of these media drastically improves the solubility of amphotericin B which otherwise has limited solubility in acetone or methanol alone.

New processes and compositions useful for the purification of amphotericin B providing a more consistent yield of highly crystalline product have been sought.

SUMMARY OF THE INVENTION

In accordance with the present invention a novel process and crystallization composition suitable for purifying amphotericin B, providing a consistently higher yield of crystalline material, are disclosed. The novel amphotericin B composition comprises amphotericin B in solution with methanol, dimethylformamide, methylene chloride and water. The novel process comprises dissolving crude, partially purified or contaminated amphotericin B in a solution of methanol, dimethylformanide and an acid; separating the resultant extract mixture from any insoluble constituents; combining the purified extract with a solvent mixture of methylene chloride and water; crystallizing the amphotericin B; and recovering the crystalline product.

DETAILED DESCRIPTION OF THE INVENTION

It has now been found that the consistency of the procedure for making amphotericin B and the crystalline nature of the product can be substantially improved by employing the quaternary solvent system of the present process. The quaternary solvent system comprises the dimethylformamide and methanol into which the amphotericin B is initially dissolved, and methylene chloride and water, which is added after filtration of the initial solution. The resulting amphotericin B crystallization composition comprises the amphotericin B, and an acid which will form a salt with the amphotericin B, in these four solvents. Additionally, it has been found that after purification, crystallization, filtering and washing, if the product is dried so as to retain at least 2 percent by weight of water and preferably between about 2 and 6 percent by weight of water, a more stable crystalline material is provided.

The table below illustrates the advantages of the present process. Shown in the table is a comparison between amphotericin B products from the Dutcher et al. process described in U.S. Pat. No. 2,908,611 and from the present process. Microbiological potency, yield, purity (as measured by residue after ignition of product), and stability were measured for each product.

|  | Microbiological Potency | Yield | Purity (residue on ignition) | Stability (activity loss/year) at 5° C. |
| --- | --- | --- | --- | --- |
| Prior Process | 884 mcg/mg | 80% | 2.5 wt percent | 10–15% |
| Present Process | 1000 mcg/mg | 97% | <0.1 wt percent | <5% |

While the exact mechanism for generating these improvements is not known, it is believed that the methylene chloride and water, which are added to the amphotericin B, methanol and dimethylformamide, enhance the crystalline structure, and thereby the microbiological activity, purity and stability of the resultant amphotericin B.

The amphotericin B employed as the starting material in the purification process may include crude, partially purified or contaminated amphotericin B. The expression "contaminated amphotericin B" is meant to include physical contaminants such as dirt particles, fibrous material and other particulate elements that might cause amphotericin B to be unacceptable for pharmaceutical utility.

The first step in the process is the extraction of the amphotericin B starting material by suspending it in a mixture of methanol and dimethylformamide together in any order and adding the acid thereto. The acid can be any acid which will readily form a salt with the amphotericin B, such as citric, hydrochloric, sulfuric, and the like. Temperature is not critical, but the extraction will preferably be carried out by adjusting the temperature of the so-formed mixture to about 15-20° C. and agitating until the amphotericin B starting material dissolved.

Separation of the extract mixture is carried out using procedures well know in the art. Preferably, filtration will be used to separate out the amphotericin B extract from insoluble materials.

The purified amphotericin B extract will thereafter be combined with a solvent mixture of methylene chloride and water. The temperatures and the order of addition of the methylene chloride and water are not critical, however the water will preferably be chilled to about 5-10° C. The pH of this mixture is adjusted to between about 5 and 7, preferably about 6, using an aqueous base, e.g. aqueous triethanolamine, or any other appropriate base. This mixture precipitates the amorphous product, and the resulting slurry (of amorphous product and solvents) provides a suitable environment for promoting the transformation of the amphotericin B into crystalline material.

The slurry of amorphous amphotericin B is converted to crystalline material by heating at a temperature of about 40° C. to about 60° C., preferably about 45° C. to about 55° C. Optionally, small amounts of seed crystals may be added to the slurry to accelerate crystallization.

Recovery of crystalline amphotericin B can be accomplished using conventional procedures; e.g., centrifugation or filtration. The isolated material can be washed with a suitable solvent, if desired, prior to drying. Preferably, the isolated crystalline material should be dried so as to retain at least 2 percent and optimally 2-6 percent by weight of water. Exemplary solvents for the washing step are acetone; mixtures of acetone and water; methanol; mixtures or methanol and water; water; or combinations thereof.

Operating conditions for executing the above described procedure may be selected in such a manner so as to yield a sterile product.

The present invention will now be described by the following Example, but is not meant to be limited by the details therein.

EXAMPLE 1

To about 565 L of methanol was added about 10 BK (base kilograms, i.e. kilograms of pure, active material) of amphotericin B and 225 L of dimethylformamide. About 18.5 KG of citric acid monohydrate (or the equivalent quantity if anhydrous acid) was added. The mixture, maintained at 15-20° C., was agitated until the input was essentially dissolved. The rich solution was then clarified by filtration.

Next, about 140 L of methylene chloride was added to the filtrate. About 225 L of water, chilled to about 5-10° C. was added. The pH was then adjusted to a pH of about 6 to precipitate the amphotericin B. Aqueous triethanolamine 40% v/v was used for the adjustment. The resulting slurry was then heated to about 44-46° C. over about 30 minutes. When the product had crystallized, as determined by microscopic examination, the mixture was cooled to about 10° C. over 2-3 hours. The purified product was then isolated by filtration and washed with about 85 L of cold 40% v/v aqueous methanol. The wet cake was then slurried in about 140 L of acetone. After filtering, the cake was washed with about 28 L of acetone and then dried to a moisture level of between 2% and 6%. About 9.7 BK of amphotericin B was recovered.

What is claimed is:

1. An amphotericin B salt forming composition comprising amphotericin B, and an acid capable of forming a salt with said amphotericin B, in a solution comprising methanol, dimethylformamide, methylene chloride in an amount sufficient to enhance the crystallinity and purity of amphotericin B produced therefrom, and water.

2. The composition of claim 1 further comprising a base suitable for adjusting the pH of said composition to between about 5 and 7.

3. A process for the purification and crystallization of amphotericin B which comprises
   a. forming a solution of amphotericin B in methanol, dimethylformamide and acid capable of forming a salt with said amphotericin B;
   b. separating amphotericin B extract from insolubles;
   c. combining said amphotericin B extract with a solvent mixture comprising methylene chloride in an amount sufficient to enhance the crystallinity and purity of amphotericin B produced therefrom, and water;
   d. adjusting the pH of the so-formed combination to between about 5 and 7;
   e. heating said slurry to expedite the formation of crystalline material; and
   f. recovering the crystalline amphotericin B.

4. A process in accordance with claim 3 wherein the recovery of the crystalline material is carried out by
   i. separating the crystalline material formed in step (e) from the remaining solvent; and
   ii. washing and drying the separated crystals, wherein the crystals are dried so as to retain between about 2 and 6 percent by weight of water.

5. A process in accordance with claim 3 wherein step (a) is carried out at between about 15° and 20° C.

6. A process in accordance with claim 3 wherein in step (a) said amphotericin B, methanol and dimethylformamide are mixed together and said acid is then added.

7. A process in accordance with claim 3 wherein said separation is done by filtration.

8. A process in accordance with claim 3 wherein in step (c) said methylene chloride is added to said extract and thereafter said water at a temperature of between about 5° and 10° C. is added to said methylene chloride and said extract.

9. A process in accordance with claim 3 wherein in step (d) the pH of the combination is adjusted to about 6.

10. A process in accordance with claim 3 wherein said slurry of step (e) is heated to between about 40° and 60° C. to convert it to crystalline amphotericin B.

* * * * *